United States Patent [19]
Chojar

[11] Patent Number: 5,081,441
[45] Date of Patent: Jan. 14, 1992

[54] HAND-HELD TONE GENERATOR FOR EQUALIZING BINAURAL HEARING AIDS

[75] Inventor: Sunil Chojar, Chanhassen, Minn.

[73] Assignee: Starkey Laboratories, Inc., Eden Prairie, Minn.

[21] Appl. No.: 630,790

[22] Filed: Oct. 30, 1990

Related U.S. Application Data

[63] Continuation-in-part of Ser. No. 464,045, Jan. 12, 1990, abandoned.

[51] Int. Cl.⁵ .................................................. G08B 3/00
[52] U.S. Cl. ................................. 340/384 E; 340/391; 128/746
[58] Field of Search ............... 340/384 E, 388, 391; 73/585; 128/746

[56] References Cited

U.S. PATENT DOCUMENTS

| | | | |
|---|---|---|---|
| 4,183,278 | 1/1980 | Rea et al. | 340/384 E X |
| 4,567,881 | 2/1986 | Heller | 128/746 X |
| 4,658,419 | 4/1987 | Denen | 340/384 E X |
| 4,688,582 | 8/1987 | Heller et al. | 128/746 |
| 4,763,355 | 8/1988 | Cox | 340/384 E X |

Primary Examiner—Donnie L. Crosland
Assistant Examiner—Brian R. Tumm
Attorney, Agent, or Firm—David H. Semmes

[57] ABSTRACT

Audible tone generators, particularly a hand-held tone generator for generating an audible tone as a test for equalizing binaural hearing aids. The circuit is characterized by its "fountain pen" size, as well as its extreme simplicity and reliability.

5 Claims, 3 Drawing Sheets

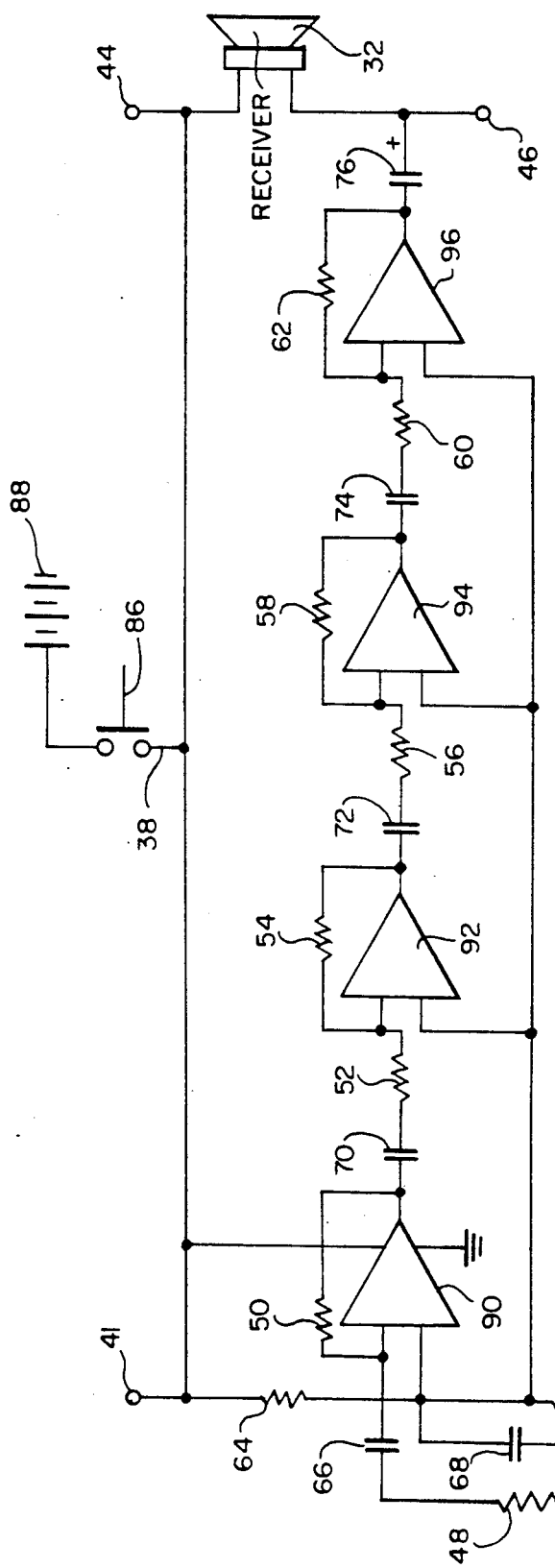
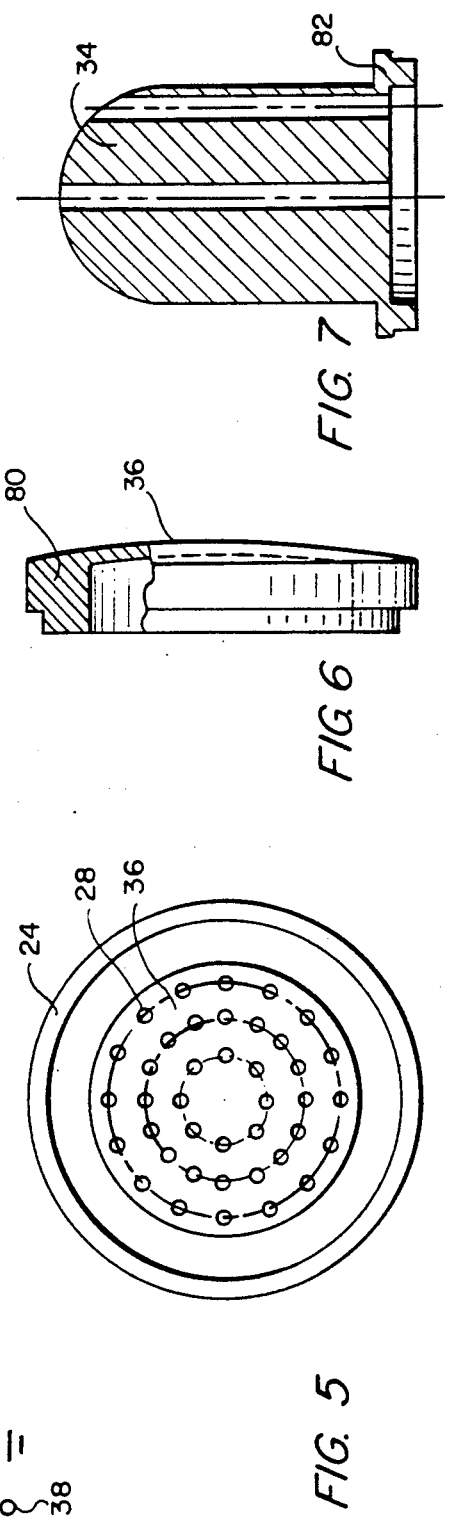
FIG. 4
FIG. 6
FIG. 7
FIG. 5

HAND-HELD TONE GENERATOR FOR EQUALIZING BINAURAL HEARING AIDS

CROSS-REFERENCES TO RELATED APPLICATIONS

A continuation-in-part of applicant's earlier filed Audible Tone Generator, Ser. No. 07/464,045, filed Jan. 12, 1990 now abandoned.

The present application concerns an improved noise amplifier circuit, which generates an audible tone for testing binaural hearing aids.

BACKGROUND OF THE INVENTION

1. Field of the Invention

Audible tone generators, particularly a hand-held device for generating a tone within the audible range as a test for human hearing.

2. Description of the Prior Art

HUTH, U.S. Pat. No. 2,156,945
MULLIN et al., U.S. Pat. No. 3,105,876
RUDMOSE, U.S. Pat. No. 3,588,358

The prior art discloses relatively bulky and complex devices for generating tones within the audible range. However, there are no prior art tone generators which are of fountain pen size and simplified format, enabling support within a coat pocket by means of a clip which serves as the on/off switch.

SUMMARY OF THE INVENTION

According to the present invention, a tone generator circuit is supported within a fountain pen type format. The fountain pen "cap" or hood includes a speaker aperture through which the generated audible tone may be amplified for testing of the human ear. The elongated fountain pen type housing supports a fountain pen type clip which enables the testing device to be carried as a fountain pen. The clip also serves as an on/off switch for closing the tone generator circuit with its source of power. The tone generator circuit is programmed to generate a broad band noise which can be used as a reference for adjusting volume on binaural hearing aids.

DESCRIPTION OF THE DRAWINGS

FIG. 4 is a circuit diagram of the operational amplifier circuit.

FIG. 5 is front elevation of the screen 36.

FIG. 6 is a side elevation of the screen.

FIG. 7 is a vertical section of socket 34 into which the amplifier circuit is fitted.

DESCRIPTION OF THE PREFERRED EMBODIMENTS

Figure 1:
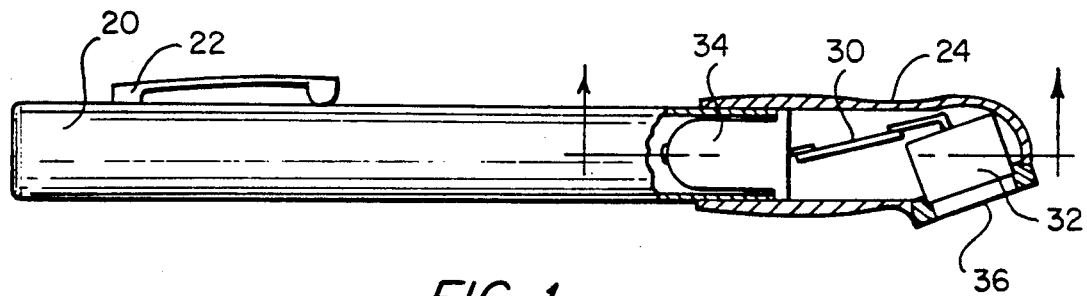
FIG. 1 is a side elevation, partially in fragmentary section of the binaural equalizer housing with attached hood.

In FIG. 1, binaural equalizer body or housing 20 is shown in the form of a fountain pen having a clip 22 which serves, also, as the on-off switch for the energizer circuit. Hood 24 is fitted to body 20, such that socket 34, printed circuit board 30, and speaker 32 may be supported therein.

As illustrated in FIGS. 1, 5 and 6, hood 24 may have a screen 36 fitted by means of shoulder 80 within the hood opening adjacent speaker 32. A plurality of apertures 28 may be provided for telephone headset-type sound channeling.

Figure 2:
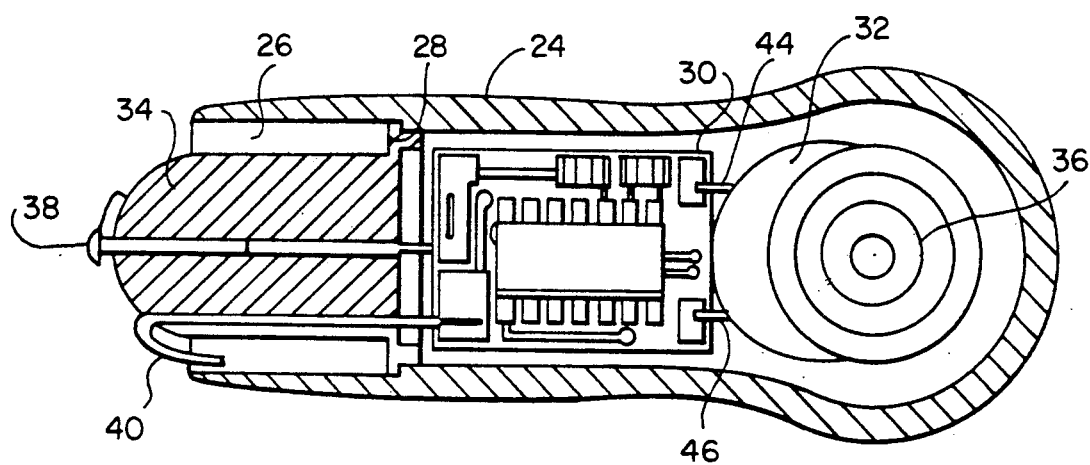
FIG. 2 is an enlarged vertical section of the hood with amplifier circuit and speaker positioned therein.
Figure 3:
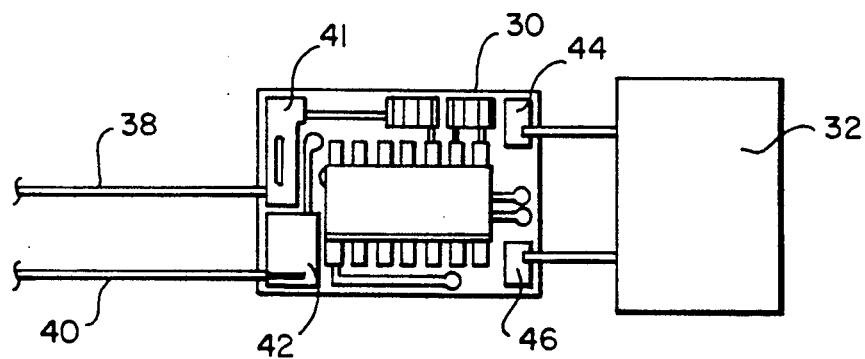
FIG. 3 is a schematic drawing of the speaker 32 and adjacent circuit board 30.
Figure 8:
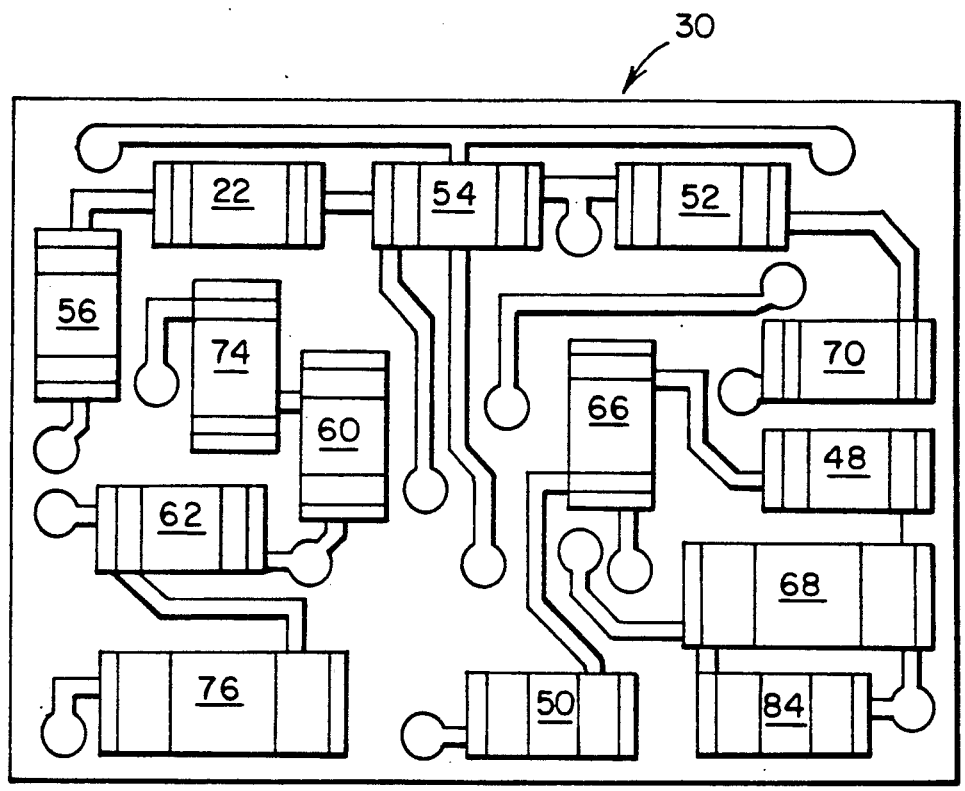
FIG. 8 is a circuit diagram of one side of the circuit board showing resistor and capacitor elements.
Figure 9:
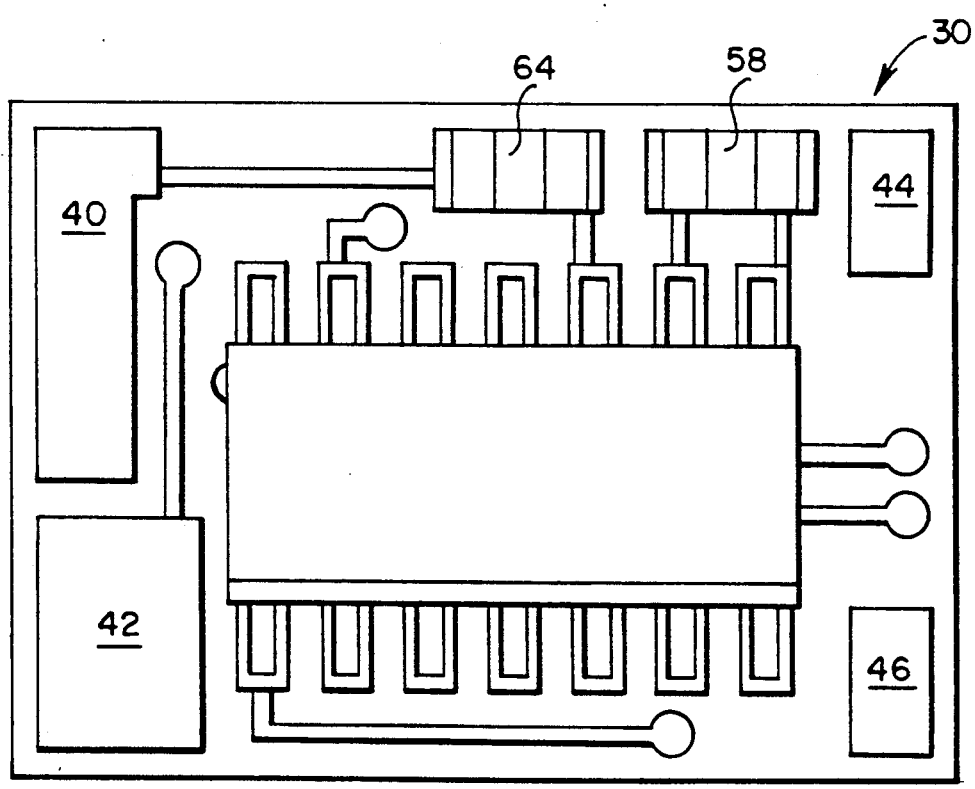
FIG. 9 is another diagram of the reverse side of the circuit board 30.

Printed circuit board 30 is illustrated in FIGS. 2 and 3 as including leads 41, 42 which engage complemental leads 38, 40 extending within socket 34. Lead 38 is in the form of a dressmaker's drape pin which contacts 3.0 volt DC (AA type) battery power supply 88 via on/off switch 86, activated by clip 22, as illustrated in FIG. 4.

The operational amplifier circuit is illustrated in FIG. 4 as including four operational amplifiers 90, 92, 94 and 96 with leads 41, 42 to the power supply and to ground. The circuit is basically a noise amplifier with each of the amplifiers providing a closed loop gain depending upon the ratio of adjacent resistors. As FIG. 4 illustrates, this circuit is basically a noise amplifier, with four LM324-type amplifiers 90, 92, 94 and 96 linked in four stages. Each stage provides a closed loop gain, depending upon the ratio of adjacent resistors. For example:

Amplifier 90 (First stage gain)=resistors 50, 48=360/15=24 dB (assumed at very high frequency)

Amplifier 92 (Second stage gain)=resistors 54, 52=360/10=36 dB

Amplifier 94 (Third stage gain)=resistors 58,56=10 dB

Amplifier 96 (Fourth stage gain)=resistors 62, 60=1.8 dB

Manifestly, the values of resistors 50, 48, 52, 54, 58, 56, 62, 60 can be varied in order to adjust the gain. The total gain is the sum of the four amplifier stages which is approximately 72 dB.

Resistors 84 and 64 supply the reference voltage to the four operational amplifiers: 90, 92, 94 and 96. Capacitor 68 stabilizes the reference voltage. The remaining capacitors 10, 12, 74, 76 serve a coupling purpose.

First stage amplifier 90 picks up noise through resistor 50 and capacitor 66, and amplifies noise through the first and remaining operational amplifier stages.

As indicated, the supply voltage of the circuit is 3.0 VDC. The total drain current is 0.45 mA.

Values of resistors may vary plus or minus 5% and capacitor tolerance may vary as much as 20%, according to the following:

Resistors:
  Resistor 50=360K
  Resistor 52=10K
  Resistor 54=360K
  Resistor 56=1K
  Resistor 58=10K
  Resistor 60=1K
  Resistor 62=1.8K
  Resistor 84=1M
  Resistor 64=1M
  Resistor 10=15K
Capacitors:
  Capacitor 66=0.047
  Capacitor 68=1.0
  Capacitor 70=0.1
  Capacitor 72=0.1
  Capacitor 74=0.1
  Capacitor 76=1.0

As illustrated in FIG. 4, the circuit leads 44, 46 are connected to receiver 32. Speaker 32 may be of a small size and light weight type manufactured by Voyagers Electronics Corp. (Intervox Series BRT1202) with the following specifications:

Rated voltage: 1.5 volts DC
Operating voltage range: 1.1 to 1.7
Current (milli-amps): 10
Direct current resistance: (Q) 42/15
Inductance (mH): 6.2
Sound pressure level (dB): M1N80 TYP 88-(10 cm)
Resonance frequency (hZ): 2040
Weight (grams): 2.

Speaker 32 provides long life at a high sound pressure level with low current consumption and without electrical noise.

It is widely recognized that even if hearing loss is mild, binaural hearing aids (i.e., one hearing aid in each ear) may provide valuable and significant improvement. With improved ability to hear correctly, stress is reduced and the user of the hearing aids will experience a relaxation of listening effort.

Applicant's binaural equalizer may be used to calibrate the binaural hearing aids. Depression of clip 22 activates on/off switch 86 to generate the broad band noise, which may be used as a reference for adjusting the individual volume on the binaural hearing aids. The user's ears, of course, must be aided equally to avoid the sensation of being "deaf" on one side. The user holds the equalizer speaker 32 adjacent the right ear (about 3 or 4 inches away) and then depresses clip 22. The process is repeated with the left ear. If the hearing aids are equal in loudness, calibration is required. If the hearing aids are unequal, one hearing aid should be turned down until the two are perceived equally.

Next, equalizer housing 20 is held facing the center of the wearer's forehead about 6 inches in front of the face. Again, clip 22 is depressed to energize the amplifier circuit. If the sound appears to be in the center of the wearer's head, no calibration is required. However, if the sound is discerned as louder on one side, then that hearing aid should be reduced in volume, correspondingly.

The user may then say "5-5-5". If the user's voice is perceived as in balance, calibration is not required. However, if the voice appears too loud, both hearing aids should be turned "down" or turned "up" correspondingly.

Ten advantages of binaural hearing have been suggested as follows:

1. Safety: when a person hears with only one ear, the difficulty in locating sound can be dangerous, especially in traffic.
2. Improved understanding: binaural hearing helps one to sort out and understand individual voices.
3. Wider hearing range: a voice barely heard at 10 feet with one ear can be heard up to 40 feet away with two ears.
4. Restful listening: listening with only one ear is physically tiring and stressful.
5. Both ears stay active: when a bilaterally hearing impaired person wears a hearing aid in only one ear, the unused ear tends to lose its ability to hear and understand.
6. Cushions loud sounds: sudden loud sounds lose much of their jarring effect when divided between two ears.
7. Better sound identification: many noises which sound almost exactly alike when heard with one ear can be identified easily when heard with two ears.
8. Smoother tone quality: binaural hearing generally requires less volume, giving a natural sound to voices and music.
9. Hearing from both sides: as nature intended, hearing with two ears allows you to enjoy a more normal social life.
10. Hear with less power: hear more quietly with less background interference.

Manifestly, variations in housing and circuitry may be employed without departing from the spirit of invention.

I claim:

1. A tone generator comprising:
   a. An elongated housing;
   b. A hood supported upon an end of said housing, including a speaker aperture;
   c. A tone generator circuit supported within the hood including:
      i. a socket adapted for connection to a source of electrical power;
      ii. a plurality of operational amplifiers whose balance is maintained by resistor and capacitor elements, and
      iii. a speaker fitted within the speaker aperture;
   d. the source of electrical power supported within said housing and connected to said tone generator circuit via said socket, and
   e. an on/off switch in the form of a resilient clip supported on the outside of said housing and interconnecting said source of electrical power and said socket.

2. A tone generator as in claim 1, including a perforated screen fitted within said hood adjacent said speaker.

3. A tone generator as in claim 2, said tone generator circuit being in the form of a printed circuit board supported within said hood intermediate said socket and said speaker.

4. A tone generator as in claim 3, said operational amplifiers being united in four stages so as to provide a total gain of approximately 72 dB.

5. A tone generator as in claim 4, said circuit having a drain current of 0.45 mA.

* * * * *